(12) United States Patent
McClintock

(10) Patent No.: US 10,365,138 B1
(45) Date of Patent: Jul. 30, 2019

(54) IN-LINE ULTRASONIC ATTENUATION END TREATMENT FOR USE WITH AN ULTRASONIC GAS FLOW METER

(71) Applicant: Big Elk Energy Systems, LLC, Tulsa, OK (US)

(72) Inventor: Dennis McClintock, Tulsa, OK (US)

(73) Assignee: Big Elk Energy Systems, LLC, Tulsa, OK (US)

( * ) Notice: Subject to any disclaimer, the term of this patent is extended or adjusted under 35 U.S.C. 154(b) by 121 days.

(21) Appl. No.: 15/589,701

(22) Filed: May 8, 2017

Related U.S. Application Data

(60) Provisional application No. 62/333,027, filed on May 6, 2016, provisional application No. 62/333,031, filed on May 6, 2016.

(51) Int. Cl.
  *G01F 1/66* (2006.01)
  *G01N 33/22* (2006.01)

(52) U.S. Cl.
  CPC .......... *G01F 1/662* (2013.01); *G01N 33/225* (2013.01); *G01N 2291/021* (2013.01); *G01N 2291/02836* (2013.01)

(58) Field of Classification Search
  CPC .. G01F 1/66; G01F 1/662; G01N 2291/02836
  USPC .......................... 73/198, 272 R, 273, 861.18
  See application file for complete search history.

(56) References Cited

U.S. PATENT DOCUMENTS

| | | | | |
|---|---|---|---|---|
| 5,090,252 A | * | 2/1992 | Tschirner | G01F 1/662 73/861.28 |
| 6,647,806 B1 | * | 11/2003 | Estrada | G01F 1/662 73/861.28 |
| 2004/0055816 A1 | * | 3/2004 | Gallagher | F16L 55/0331 181/256 |

* cited by examiner

*Primary Examiner* — Benjamin R Schmitt
(74) *Attorney, Agent, or Firm* — Gable Gotwals

(57) ABSTRACT

An end treatment for use with an ultrasonic gas flow meter includes an attenuation section having a pipe extending in a longitudinal direction and containing a set of alternating, spaced, and vertically oriented first and second plates located between an inlet end and an outlet end of the pipe. Each plate includes a first end connected to an inside wall of the pipe and a second end extending past a longitudinal centerline of the pipe to define a gap between the end of the plate and a respective opposing inside wall of the pipe. As the gas traverses the plates by flowing through the gaps, the ultrasonic waves are prevented from reflecting back to the flow meter.

22 Claims, 4 Drawing Sheets

IN-LINE ULTRASONIC ATTENUATION END TREATMENT FOR USE WITH AN ULTRASONIC GAS FLOW METER

CROSS REFERENCE TO CO-PENDING APPLICATIONS

This application claims priority to U.S. 62/333,027 and U.S. 62/333,031, both filed May 6, 2016.

BACKGROUND

This disclosure relates to gas flow measurement equipment and, in particular, to equipment, systems, and methods designed to improve the accuracy of gas flow measurement in custody transfer transactions along a gas pipeline. Because of the tremendous volume of gas being transferred between pipeline companies, small measurement errors can have very large financial effects.

To measure gas flow through a pipeline, ultrasonic gas flow meters are placed along a section of pipe. A front end treatment or elbow diverts the main pipeline flow toward the flow meter and reduces swirl using a flow conditioner placed 10 pipeline diameters ahead of the flow meter. The conditioner provides a bullet-nosed gas flow profile into the meter. A backend treatment or elbow located at least 5 pipeline diameters after the meter brings the now-measured gas flow back in line with the main pipeline (see FIG. 1). The backend elbow, along with a blind flange located opposite the main pipeline, helps attenuate ultrasonic waves generated by downstream equipment such as a control valve and prevents those waves from traveling back to the flow meter and interfering with flow measurement.

The use of elbows at the front and back end of the flow meter section widens the footprint of the section. Therefore, a wide skid must be built to support the section and special permits must be obtained to transport the skid to the job site. A need exists for an ultrasonic attenuation treatment that can eliminate the use of elbows.

SUMMARY

Embodiments of an end treatment for use with an ultrasonic gas flow meter include an attenuation section having a pipe extending in a longitudinal direction and containing a set of alternating, spaced, and vertically oriented first and second plates located between an inlet end and an outlet end of the pipe. Each plate includes a first end connected to an inside wall of the pipe and a second end extending past a longitudinal centerline of the pipe to define a gap between the end of the plate and a respective opposing inside wall of the pipe. As the gas traverses the plates by flowing through the gaps, the ultrasonic waves reflect off the plates, toward other plates or the pipe wall and not back to the ultrasonic gas flow meter.

In some embodiments, the first plates extend from a top inside wall of the pipe and the second plates extend from the bottom inside wall of the pipe. The second plates, when arranged as bottom plates, may include a mouse hole located toward the first end to prevent pooling of condensate.

The inlet and outlet ends may have a first inside diameter D1 and a second inside diameter D2, D2>D1, with the pipe being at the second inside diameter D2. The gap can be sized to be less than the first inside diameter D1. In some embodiments, the gap is sized to half that of the first inside diameter D1. The second inside diameter D2 may be at least twice that of the first inside diameter D1. The inlet end can be arranged for D1 to D2 flow and the outlet end can be arranged for D2 to D1 flow. The inlet and outlet ends may include an eccentric reducer.

A method of attenuating ultrasonic waves originating from downstream of the ultrasonic gas flow meter is also disclosed. Embodiments of the method include causing a gas flow that exits the ultrasonic gas flow meter to traverse an attenuation section that includes a pipe extending in a longitudinal direction and containing a set of alternating, spaced, and vertically oriented first and second plates located between an inlet end and an outlet end of the pipe, wherein each plate includes a first end connected to an inside wall of the pipe and a second end extending past a longitudinal centerline of the pipe to define a gap between the end of the plate and a respective opposing inside wall of the pipe.

ELEMENTS AND NUMBERING USED IN THE DRAWINGS AND DETAILED DESCRIPTION

Figure 1:
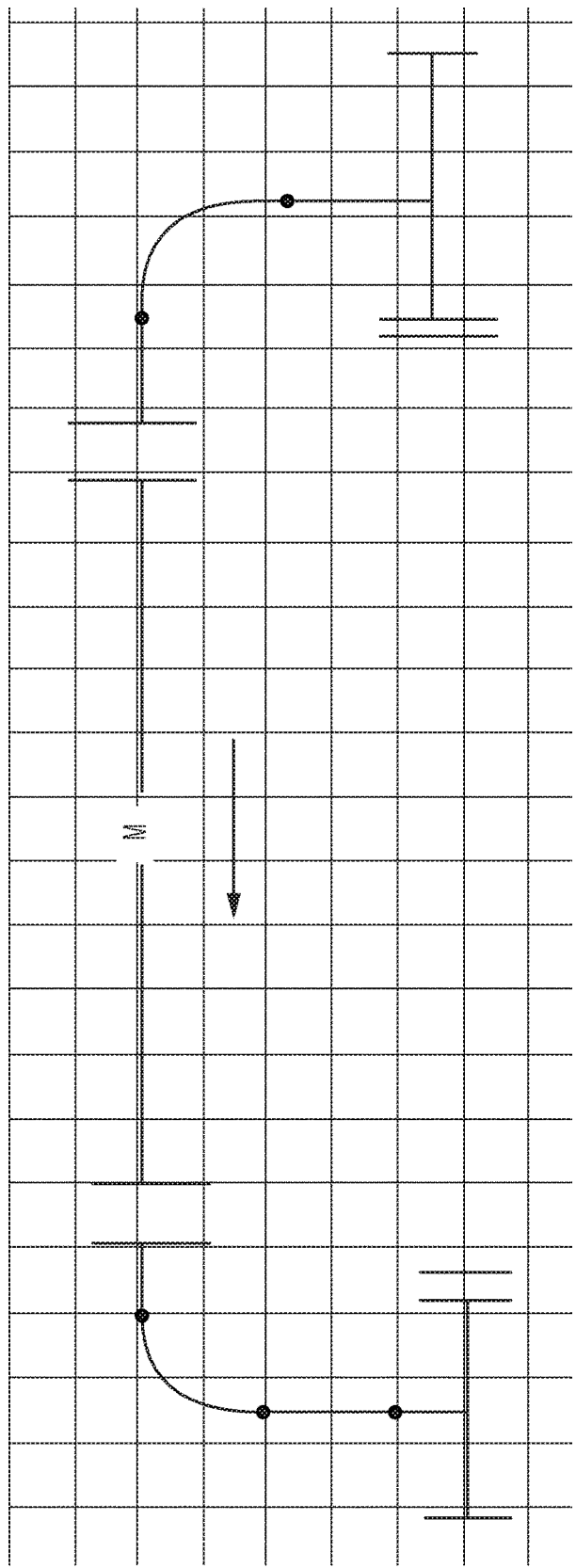
FIG. 1 is a prior art gas flow meter or measurement section of a gas pipeline.
Figure 2:
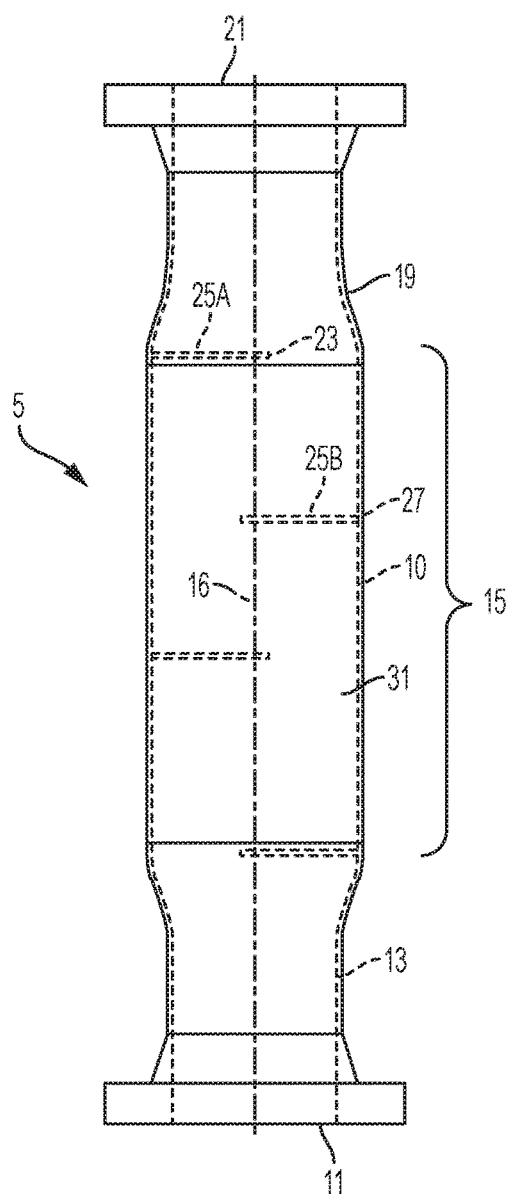
FIG. 2 is top plan view of an embodiment of an inline ultrasonic attenuation end treatment.
Figure 3:
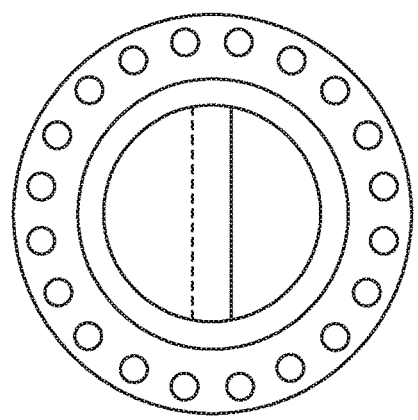
FIG. 3 is an end view of the end treatment.
Figure 4:
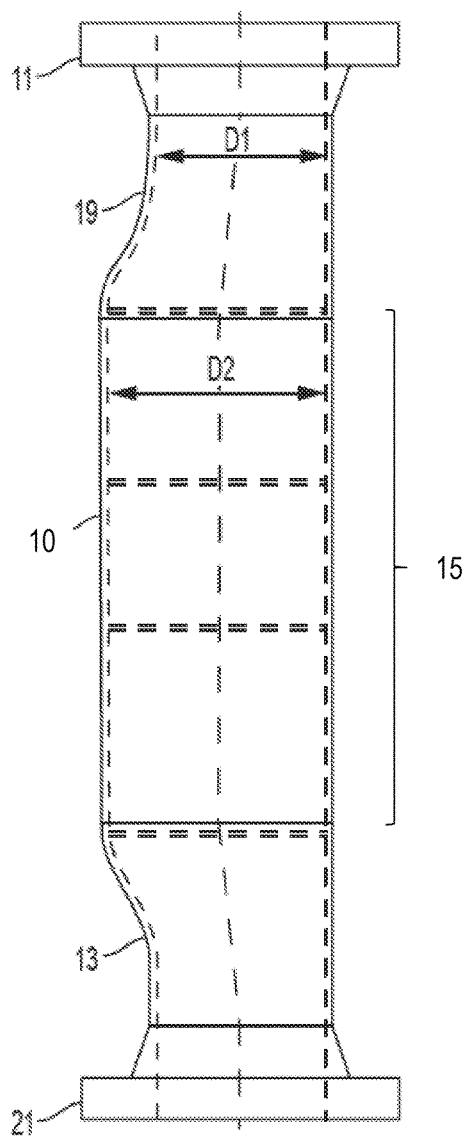
FIG. 4 is a side elevation view of the end treatment.
Figure 5A:
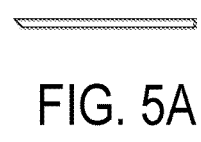
FIG. 5A is an embodiment of a reflective plate having a 45° bevel on the radial edge of the plate.
Figure 5B:
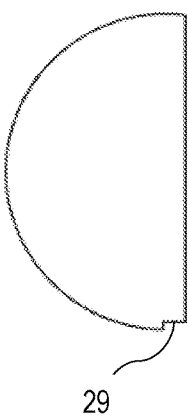
FIG. 5B is a front elevation view of a notch or mouse hole located toward a pipe wall end of a reflective plate.

5 Inline ultrasonic attenuation end treatment
10 Pipe section
11 Inlet end having a first inside diameter D1
13 Reducer located toward 11 (e.g. 12" to 16")
15 Attenuation section (e.g. 16")
16 Longitudinal centerline
19 Reducer located toward 21 (e.g. 16" to 12")
21 Outlet end
23 Second (inward) end of 25
25 Plate
27 First (pipe wall) end of 25
29 Mouse hole
31 Gap
35 Effects isolator
40 Flow conditioner
41 Perforated plate
43 Central aperture
45 Aperture array
50 Tube bundle
53 Central vane
55 Vane bundle or array
D1 First inside diameter
D2 Second inside diameter

DETAILED DESCRIPTION

In embodiments of an inline ultrasonic attenuation end treatment 5, ultrasonic waves are prevented from interfering with an ultrasonic gas flow meter by a series of alternating plates.

Referring first to FIGS. 2 to 5B, the end treatment 5 includes a pipe section 10 with two different size inside diameters D1, D2 located between and inlet end 11 and outlet end 21, with D2>D1. The ends 11, 21, which may be arranged for connection to a respective opposing end of a main pipeline, have the first inside diameter D1. Located between the two ends 11, 21 are eccentric reducers 13, 19 and an attenuation section 15. (Concentric reducers may be used but eccentric reducers can prevent puddling.) Eccentric reducers 13, 19 also have the second inside diameter D2. Reducer 13 is arranged for D1 to D2 flow. Reducer 19 is arranged for D2 to D1 flow.

Attenuation section 15 also has second inside diameter D2 extending along its entire length and includes a set of alternating, horizontally spaced, and vertically oriented plates 25A, 25B. In embodiments, plates 25A are top plates and plates 25B are bottom plates. The second (inward) end 23 of the plate 25 can be beveled and the first (pipe wall) end 27 may include a mouse hole 29 for drainage.

The attenuation section 15 may be sized so that an effective inside diameter provided by a set of two alternating plates 25A, 25B is the same as that of the first inside diameter D1. Each plate 25 can extend past the section's longitudinal centerline 16 to eliminate any straight line path back to the flow meter. Therefore, to reach the ultrasonic gas flow meter and interfere with its measurement, any ultrasonic wave being reflected back toward the flow meter must traverse the set of alternating reflective plates 25. However, each plate 25 causes the wave to reflect back to an adjacent plate 25 or the pipe wall The inline ultrasonic attenuation end treatment 5 can be used in combination with a front end treatment including an effects isolator. The effects isolator can eliminate the need for end treatment upstream of the ultrasonic flow meter and can be used in combination with the in-line ultrasonic attenuation treatment end.

Figure 6:
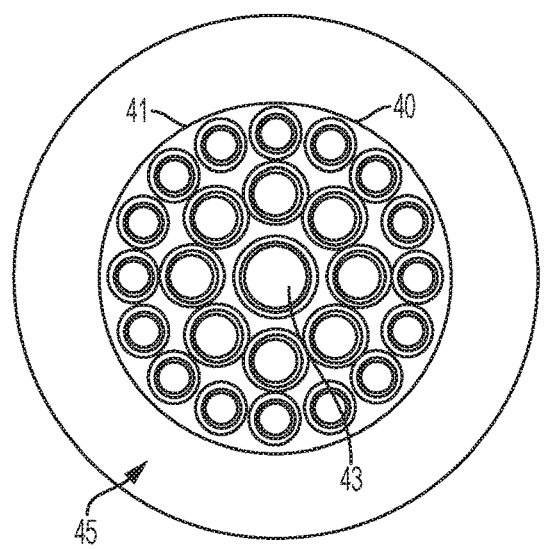
FIG. 6 is front elevation view of an embodiment of an effects isolator that may be used as part of an inline front end treatment in combination with the inline ultrasonic attenuation end treatment.
Figure 7:
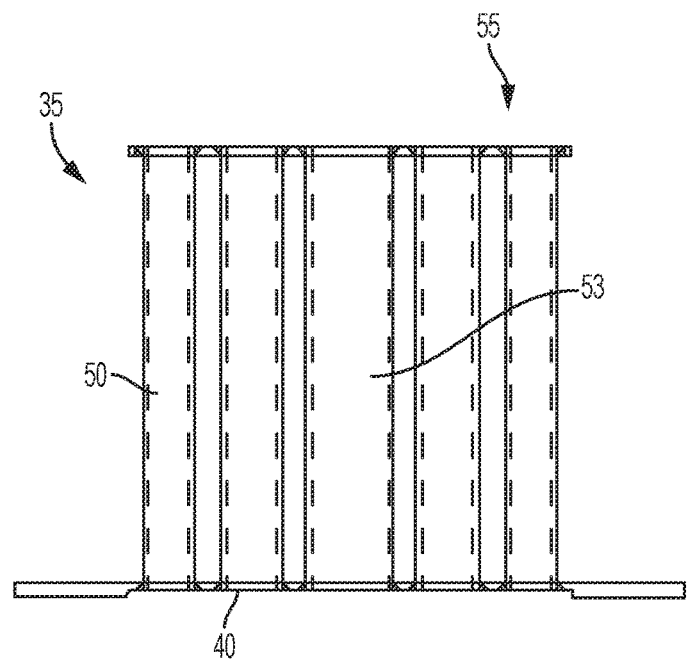
FIG. 7 is top plan view of the effects isolator.

Referring now to FIGS. 6 and 7, embodiments of an effects isolator 35 may include a flow conditioner 40 or a flow conditioner 40 connected to or spaced from a tube bundle 50. The flow conditioner 40 may be the same or similar to that disclosed in U.S. Pat. No. 5,341,848 and include a perforated plate 41 having a central aperture 43 with one or more apertures 45 arrayed about it. The flow conditioner 40 can help develop the desired bullet-nosed flow profile for flow into the ultrasonic gas flow meter. Similar to the attenuation end treatment, the front end treatment may be an in-line treatment end.

The tube bundle 50 may include a longitudinally extending central vane 53 corresponding to the central aperture 43 of the flow conditioner 40 and a bundle or array of longitudinally extending vanes 55 arranged about the central vane 53. The size and number of vanes 45 correspond to a respective size and number of apertures 45 in the flow conditioner 10. Preferably, the vanes 53, 55 are about the same diameter as the flow conditioner's 40 perforations.

Although embodiments an inline ultrasonic attenuation end treatment have been described with reference to particular means, materials and embodiments, the end treatment is not intended to be limited to those particulars. Rather, the description extends to all functionally equivalent structures, methods, and uses, such as are within the scope of the following claims.

What is claimed:

1. An end treatment for use with an ultrasonic gas flow meter, the end treatment comprising:
   an ultrasonic wave attenuation section including a pipe extending in a longitudinal direction and containing a set of alternating, spaced, semi-circular shaped, and vertically oriented first and second plates located between an inlet end and an outlet end of the pipe;
   each plate including a first end connected to an inside wall of the pipe, a second end extending past a longitudinal centerline of the pipe to define a gap between the second end of the plate and a respective opposing inside wall of the pipe, and a solid wall surface extending an entire distance between the first and second ends.

2. The end treatment of claim 1 wherein the first plates extend from a top inside wall of the pipe and the second plates extend from the bottom inside wall of the pipe.

3. The end treatment of claim 2 further comprising the second plates including a mouse hole located toward the first end.

4. The end treatment of claim 1 further comprising the inlet and outlet ends including a first inside diameter D1 and the pipe including a second inside diameter D2, D2>D1.

5. The end treatment of claim 4 further comprising the gap sized to be less than the first inside diameter D1.

6. The end treatment of claim 5 further comprising the gap sized to half that of the first inside diameter D1.

7. The end treatment of claim 4 wherein the second diameter D2 is at least twice that of the first inside diameter D1.

8. The end treatment of claim 4 wherein the inlet end is arranged for D1 to D2 flow and the outlet end is arranged for D2 to D1 flow.

9. The end treatment of claim 4 further comprising the inlet and outlet ends including an eccentric reducer.

10. The end treatment of claim 1, the second end being a straight end.

11. An end treatment for use with an ultrasonic gas flow meter, the end treatment comprising:
    an ultrasonic wave attenuation section including a pipe extending in a longitudinal direction and containing a set of alternating, spaced, semi-circular shaped, and vertically oriented first and second plates located between an inlet end and an outlet end of the pipe;
    the inlet and outlet ends including a reducer with a first inside diameter D1 and a second inside diameter D2, the pipe including the second inside diameter D2, the inlet end arranged for D1 to D2 flow, the outlet end arranged for D2 to D1 flow, D2>D1;
    each plate including a first end connected to an inside wall of the pipe, a second end extending past a longitudinal centerline of the pipe to define a gap between the second end of the plate and a respective opposing inside wall of the pipe, and a solid wall surface spanning an entire distance between the first and second ends, wherein the gap is sized less than D1.

12. The end treatment of claim 11 wherein the first plates extend from a top inside wall of the pipe and the second plates extend from the bottom inside wall of the pipe.

13. The end treatment of claim 12 further comprising the second plates including a mouse hole located toward the first end.

14. The end treatment of claim 12 further comprising the gap sized to half that of the first inside diameter D1.

15. The end treatment of claim 12 wherein the second diameter D2 is at least twice that of the first inside diameter D1.

16. The end treatment of claim 15 further comprising the inlet and outlet ends including an eccentric reducer.

17. The end treatment of claim 11, the second end being a straight end.

18. A method of attenuating ultrasonic waves originating from a downstream source, the method comprising:
   causing a gas flow exiting an ultrasonic gas flow meter to traverse an ultrasonic wave attenuation section that includes a pipe extending in a longitudinal direction and containing a set of alternating, spaced, semi-circular shaped, and vertically oriented first and second plates located between an inlet end and an outlet end of the pipe;
   wherein each plate includes a first end connected to an inside wall of the pipe, a second end extending past a longitudinal centerline of the pipe to define a gap between the second end of the plate and a respective opposing inside wall of the pipe, and a solid wall surface extending an entire distance between the first and second ends.

19. The method of claim 18 wherein the first plates extend from a top inside wall of the pipe and the second plates extend from the bottom inside wall of the pipe.

20. The method of claim 19 wherein the gap is sized less than the first inside diameter D1.

21. The method of claim 18 wherein the inlet and outlet ends include a reducer with a first inside diameter D1 and a second inside diameter D2, the pipe including the second inside diameter D2, the inlet end arranged for D1 to D2 flow, the outlet end arranged for D2 to D2 flow, D2>D1.

22. An end treatment for use with an ultrasonic gas flow meter, the end treatment comprising:
   an ultrasonic wave attenuation section including a pipe extending in a longitudinal direction and containing a set of alternating, spaced, semi-circular shaped, and vertically oriented first and second plates located between an inlet end and an outlet end of the pipe;
   each plate including a first end connected to an inside wall of the pipe, a second end extending toward a respective opposing inside wall of the pipe to define a gap between the second end of the plate and the respective opposing inside wall of the pipe, and a solid wall surface extending an entire distance between the first and second ends.

\* \* \* \* \*